United States Patent
Deng et al.

(10) Patent No.: US 8,835,680 B1
(45) Date of Patent: Sep. 16, 2014

(54) STEREOSPECIFIC SYNTHESIS PROCESS FOR TRETINOIN COMPOUNDS

(75) Inventors: Qingjun Deng, Chongqing (CN); Shaohui Wang, Chongqing (CN); Qiang Zhu, Chongqing (CN); Taiping Gao, Chongqing (CN); Yongsheng Li, Chongqing (CN)

(73) Assignee: Chongqing Huabangshengkai Pharm. Co., Ltd., Chongqing (CN)

( * ) Notice: Subject to any disclaimer, the term of this patent is extended or adjusted under 35 U.S.C. 154(b) by 0 days.

(21) Appl. No.: 14/117,343

(22) PCT Filed: May 7, 2012

(86) PCT No.: PCT/CN2012/075130
§ 371 (c)(1),
(2), (4) Date: Nov. 12, 2013

(87) PCT Pub. No.: WO2012/155796
PCT Pub. Date: Nov. 22, 2012

(30) Foreign Application Priority Data

May 13, 2011 (CN) .......................... 2011 1 0124227

(51) Int. Cl.
 C07C 61/16 (2006.01)
 C07C 53/134 (2006.01)
 C07C 51/00 (2006.01)

(52) U.S. Cl.
 CPC ..................................... *C07C 51/00* (2013.01)
 USPC ......................................... 562/510; 562/496

(58) Field of Classification Search
 USPC ................................................. 562/496, 510
 See application file for complete search history.

(56) References Cited

U.S. PATENT DOCUMENTS

| 3,932,485 A | 1/1976 | Surmatis |
| 4,215,215 A | 7/1980 | Bollag et al. |
| 5,504,230 A | 4/1996 | John et al. |

FOREIGN PATENT DOCUMENTS

| CN | 1771227 A | 5/2006 |
| CN | 101774954 A | 7/2010 |
| CN | 101987840 A | 3/2011 |
| DE | 1059900 B | 6/1959 |
| EP | 0 659 739 A1 | 6/1995 |
| WO | 2011/015101 A1 | 2/2011 |

OTHER PUBLICATIONS

W. J. Burke., et al "Study of 2-Naphthol-Hexamethylenetetramine Condensation Products" Journal of the American Chemical Society, Feb. 1956, vol. 78, p. 808.
46. Neue Zugange zu einigen aromatischen Retinoiden, Helvetica Chimica Acta, 1989, vol. 72, p. 370-376.

*Primary Examiner* — Jafar Parsa
(74) *Attorney, Agent, or Firm* — Maschoff Brennan

(57) ABSTRACT

A stereospecific synthesis process for tretinoin compounds comprises the following steps: using substituted triphenyl phosphine salt and β-formyl crotonic acid as raw material to carry out WITTIG reaction under the action of alkali; then adjusting the pH of the reaction liquid to 5-10; adding palladium compound or rhodium compound to carry out isomerization directly and obtain tretinoin compounds with desired configuration. The product yield of the process is high and the intermediate product in the reaction dose not need to be separated. The process is easy to operate and can save the production cost and as well is suitable for industrial production.

10 Claims, No Drawings

STEREOSPECIFIC SYNTHESIS PROCESS FOR TRETINOIN COMPOUNDS

TECHNICAL FIELD OF THE INVENTION

The invention relates to a stereospecific synthesis process for tretinoin compounds, specifically to the synthesis process for the tretinoin compounds with configuration including conjugated unsaturated carboxylic acid, substituted unsaturated hexatomic carbon ring and multiple conjugated double bonds.

BACKGROUND OF THE INVENTION

Tretinoin is metabolite of vitamin A and used widely for curing psoriasis and acne clinically with significant effects. After all-trans tretinoin (Formula Ia) was developed, other various compounds with similar configuration are developed, such as isotretinoin (Formula Ib), acitretin (Formula Id), alitretinoin (Formula Ic) and etc., which are also used for curing psoriasis and acne. The common features of these tretinoin compounds are that, their configurations all include configuration including conjugated unsaturated carboxylic acid, substituted unsaturated hexatomic carbon ring, multiple conjugated double bonds, and they all have specific stereo configurations.

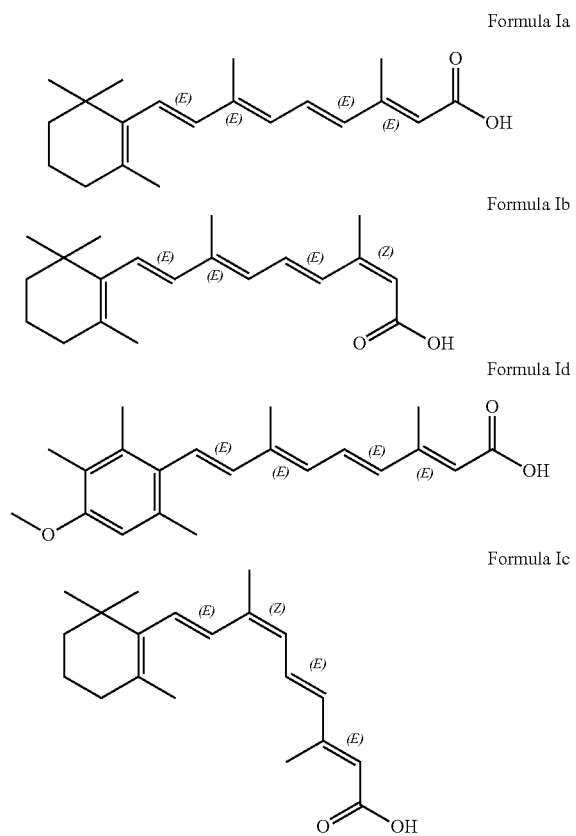

In the process of preparing tretinoin compounds, it's required to consider two important questions: the first one is how to form the group "conjugated unsaturated carboxylic acid"; the second one is how to control the stereo configuration of product. For example, the configurations of both tretinoin (Formula Ia) and acitretin (Formula Id) are all 2,4,6,8- all trans; the configurations of isotretinoin (Formula Ib) is 2-cis, 4-trans, 6-trans, 8-trans; that of alitretinoin (Formula Ic) is 2-trans, 4-trans, 6-cis, 8-trans.

In prior processes of preparation, the group "conjugated unsaturated carboxylic acid" in tretinoin compounds generally is obtained by generating the corresponding ester firstly and then hydrolyzing the ester. However, the hydrolysis process may aggravate the diversification of stereo configuration of products and generate other impurities, which makes post-treatment complicated. In order to gain end product with desired configuration, multiple recrystallization or column chromatography is generally adopted, which are not only complex but also with lower yield.

For instance, in DE1059900, the preparation process of all-trans tretinoin is as following: carrying out WITTIG reaction with [3-methyl-5-(2,6,6-trimethylcyclohexene-1-yl)-2,4-pentadiene]-triphenyl phosphonate (Formula IIa) and β-formyl crotonicacid ester (Formula IV) as raw materials; then adding alkali for hydrolysis; after hydrolysis, sequentially performing acidification, extraction and recrystallization for twice to obtain all-trans tretinoin with yield of 25-30%.

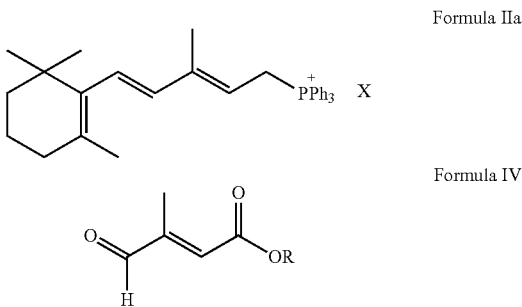

This process is complex with multiple steps; furthermore, since there are various cis isomers generated in WITTIG reaction and hydrolysis reaction, the yield is very low.

In the process for preparation acitretin in U.S. Pat. No. 4,215,215, firstly obtaining ester by [5-(4-methoxy-2,3,6-trimethyl-phenyl)-3-methyl-2,4-pentadiene]-triphenyl phosphonium bromide (Formula IId) reacting with β-formyl crotonicacid ester (Formula IV), then adding alkali for hydrolysis, carrying out acidification and extraction in sequence to gain acitretin.

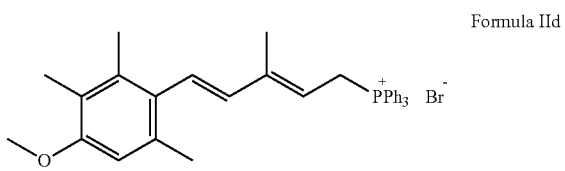

The ester obtained in this process have to be hydrolyzed after separation and purification, which is also complex and with low yield.

Therefore, a process with simple synthesis method and high product yield for preparation of tretinoin compounds is desiderated.

SUMMARY OF THE INVENTION

The invention is directed to a process for preparing the compound of Formula I, which is of low cost, high yield, less and simple steps, and is easy for industrial production.

The preparation process of the compound in Formula I disclosed in the invention comprises: performing WITTIG reaction under the action of alkali with the substituted triphenyl phosphonate (formula II) and β-formoxyl crotonic acid (formula III) as raw materials; then performing isomerization by adding palladium compound or rhodium compound to obtain the product compound of formula I with desired configuration, characterized in that:
1) there is no need to perform hydrolysis after the WITTIG reaction;
2) there is no need to separate the products of WITTIG reaction, but performing isomerization directly; the WITTIG reaction and the isomerization are conducted continuously in one container;
3) adjusting the pH of reaction liquid to 5-10 by adding acid before the isomerization;

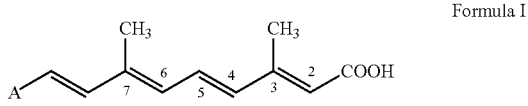

Formula I in Formula I, the carbon-carbon double bonds on site 2-3, site 4-5 and site 6-7 have cis or trans configuration;

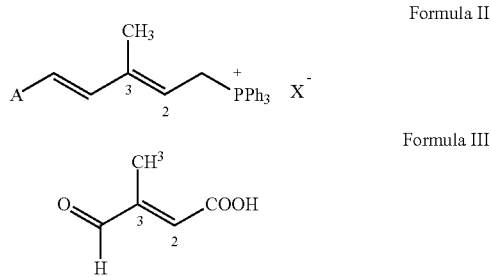

Formula II

Formula III the carbon-carbon double bonds on site 2-3 in both Formula II and Formula III have cis or trans configuration;
in Formula I and Formula II, A is substituted unsaturated hexatomic carbocyclic group; X is selected from Cl, Br or $HSO_4$.

Preferably, A is 2,6,6-trimethylcyclohexenyl or 2,3,6-trimethyl-4-methoxyphenyl.

The process research in present invention:
1. Condition Research of WITTIG Reaction The first step of the process in present invention: carrying out WITTIG reaction between compounds in Formula II and Formula III, i.e., the carbonyl in Formula III is transformed to carbon-carbon double bond to link to Formula II.
1) The molar ratio of compounds in Formula II and Formula III is 1:0.8-1.5.
2) Temperature of WITTIG reaction is −50-30° C., and preferably the reaction temperature is −5-5° C.
3) Time of WITTIG reaction is 1-24 hours, and preferably the reaction time is 3-4 hours.
4) Alkali
the alkali is the substance as long as it can make reaction system alkaline, and preferably, it's alkaline metal salt of $C_1$-$C_6$ alkyl alcohol or metal hydroxide, such as sodium methylate, potassium methoxide, lithium methoxide, sodium ethoxide, potassium ethoxide, potassium isopropoxide, potassium tert-butoxide, sodium hydroxide, potassium hydroxide, lithium hydroxide and so on, preferably it's potassium hydroxide.

2. Condition Research of Isomerization Reaction

In the process of this invention, when carrying out the WITTIG reaction between compounds of Formula II and Formula III, the new-generated carbon-carbon double bond will form cis isomers and trans isomers.

Thus, in order to obtain end product with specific configuration, it's required to carry out further isomerization reaction. The purpose of isomerization reaction is to make the cis isomers of new-generated carbon-carbon double bond transformed to trans isomers effectively.

In experiments, the inventor of this invention finds that, before carrying out isomerization, the pH of reaction system is significantly important to transformation rate of the isomerization on the next step; it will influence the transformation if the pH is too low, while it will generate impurities easily if the pH is too high. Therefore, it is critical to control the range of pH in this step for high transformation rate and products yield. Before isomerization, adding acids can strictly control the desired pH.

1) the Optimum pH Research of Isomerization (See Embodiment 1-3, pH Comparative Experiments Example 1-2)

The said acid is inorganic acid or organic acid, wherein inorganic acid is selected from sulphuric acid, hydrochloric acid, phosphoric acid, hydrobromide and so on; said organic acid is $C_1$-$C_6$ alkyl acid, such as formic acid, acetic acid, propionic acid, butyric acid etc., preferably hydrochloric acid; the amount of acid is for adjusting pH of reaction system to 5-10, and preferably pH is 7-8.

2) Catalyst Selection of Isomerization (See Embodiment 4-7)

Catalyst is palladium compound or rhodium compound, which is selected from $PdCl_2$, $PdBr_2$, $PdI_2$, $PdF_2$, PdS, $(CH_3CN)_2PdCl_2$, $Pd(OAc)_2$, $(PhCN)_2PdCl_2$, $Pd(NO_3)_4(NH_4)_2$, $Pd(NH_3)_2Cl_2$, $PdS_2$, $K_2PdCl_6$, $Pd(NH_3)_2(NO_2)_2$, $Pd(NO_2)_4(NH_3)_2$, $(PhCN)_2PdBr_2$, $(NH_4)_2PdCl_4$, $NH_4)_2PdCl_6$, $(Ph_3P)_4Pd(0)$, $(Et_3P)_4Pd(0)$, $(Ph_3P)_3PdCl_2$, $Pd(NO_3)_2 +Ph_3P$, the same salts or complexes of palladium or rhodium can also be used. The effect of $Pd(OAc)_2$ is better. The compounds of palladium or rhodium include complexes including palladium or rhodium.

3) Catalyst Amount in Isomerization Reaction

The molar ratio between the amounts of said compounds of palladium or rhodium and compound of Formula II is 0.0001-0.02:1.

4) Temperature of Isomerization Reaction (See Embodiment 1, 8-10, Temperature Comparative Experiments)

Isomerization temperature also has influence on isomerization; isomerization speed is slow if temperature is low. Isomerization speed is fast if temperature is high, but with more impurities. The preferable temperature of isomerization is 30° C.-80° C., more preferably 50° C.-60° C.

5) Time of Isomerization Reaction

There is no specifically requirement on time of isomerization. It can be monitored by high performance liquid chromatography (HPLC) till the isomerization is finished. The standard to judge whether isomerization is finished is that, the relative proportion of the non-isomerized material is less than 3% detected via HPLC.

6) Methods of Monitoring Whether Isomerization Reaction is Finished

HPLC of monitoring whether isomerization is finished is as follows: chromatographic column: Waters ODS (4.6×150 mm, 3 μm), mobile phase:methanol:water:glacial acetic acid=800:225:5; velocity of flow: 1 ml/min, temperature of column: 30° C., detection wavelength: 355;

7) Methods of Product Post-Treatment

When isomerization is finished, its reaction mixture is poured into water, neutralized with acid, filtrated to gain crude product and crystallized to obtain product.

The concrete applications of the process in this invention are demonstrated in following reaction formulas:

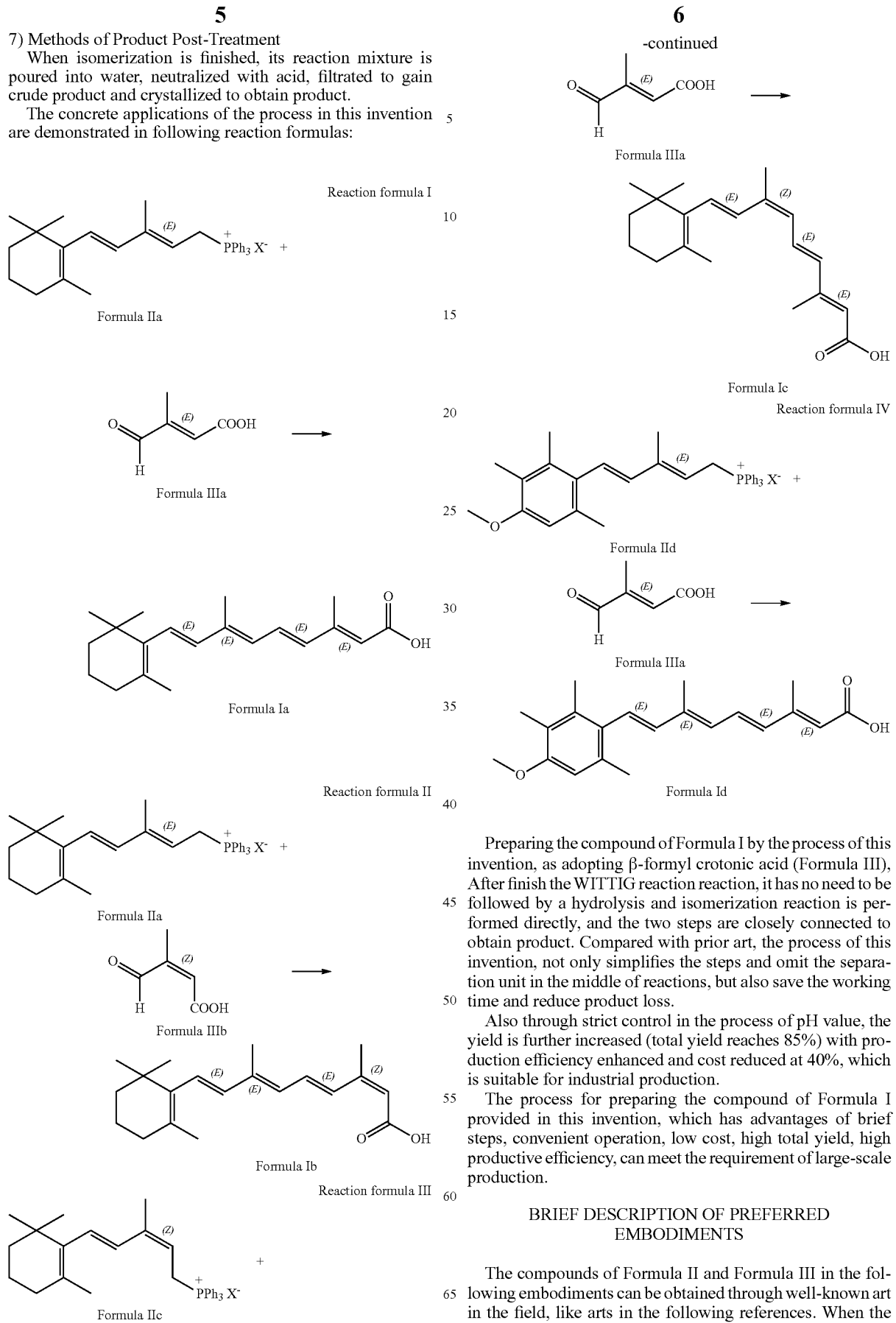

Preparing the compound of Formula I by the process of this invention, as adopting β-formyl crotonic acid (Formula III), After finish the WITTIG reaction reaction, it has no need to be followed by a hydrolysis and isomerization reaction is performed directly, and the two steps are closely connected to obtain product. Compared with prior art, the process of this invention, not only simplifies the steps and omit the separation unit in the middle of reactions, but also save the working time and reduce product loss.

Also through strict control in the process of pH value, the yield is further increased (total yield reaches 85%) with production efficiency enhanced and cost reduced at 40%, which is suitable for industrial production.

The process for preparing the compound of Formula I provided in this invention, which has advantages of brief steps, convenient operation, low cost, high total yield, high productive efficiency, can meet the requirement of large-scale production.

BRIEF DESCRIPTION OF PREFERRED EMBODIMENTS

The compounds of Formula II and Formula III in the following embodiments can be obtained through well-known art in the field, like arts in the following references. When the compound of Formula II is trans, A is 2,6,6-trimethyl cyclohexenyl: U.S. Pat. No. 3,932,485. When the compound of Formula II is cis, A is 2,6,6-trimethyl cyclohexenyl: U.S. Pat. No. 3,932,485, EP0659739.

When the compound of Formula II is trans, A is 4-methoxy-2,3,6-trimethyl-phenyl: Helvetica Chimica Acta, 1989, vol. 72, p 370-376.

The compound of Formula III can be obtained by purchasing or well-known art. For example, if the compound of Formula III is trans, it can be purchased from Aladdin Agent Co., Ltd. or obtained by the process in CN101987840A.

When the compound of Formula III is cis, it can be obtained by process defined in the reference of Journal of the American Chemical Society, 1956, vol. 78, p 808.

Embodiment 1-10

Preparation for 3,7-dimethyl-9-(2,6,6-trimethylcyclohexene-1-yl)-2E, 4E, 6E, 8E-nonatetraenoic acid

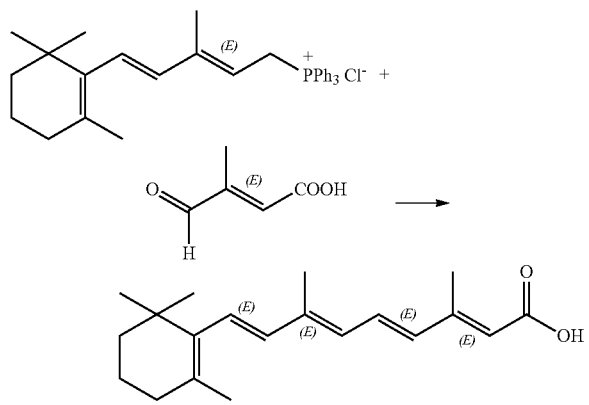

Operation Process and Reaction Condition of Embodiment 1:

186 g [3-methyl-5-(2,6,6-trimethylcyclohexene-1-yl)-2E, 4E-pentadiene]-triphenyl phosphonic chloride was dissolved in 500 ml isopropanol; 42.3 g trans-β-formyl crotonic acid was added with nitrogen filling and the mixture was stirred to be transparent. When temperature was decreased to −5-0° C., 571 ml KOH isopropanol solution with concentration 2N was added drop wise. The temperature was kept at −5-0° C. for 2 hours for reaction; the pH was adjusted to 7-8 with hydrochloric acid, and 86 mg palladium acetate was added to the reaction mixture; then the temperature was increased to 50° C.

Through HPLC detection, it's detected that, when isomerization was finished, the reaction mixture was poured into water, neutralized by adding concentrated hydrochloric acid, filtrated to gain crude product of the captioned product, crystallized by ethyl acetate to obtain 95.2 g product with purity of 99.7% and yield of 85.3%.

The operation of embodiment 2-9 was the same of embodiment 1. However, their reaction results were compared with various reaction conditions changed.

Embodiment 2, 3 and Example 1, 2 of pH Comparative Experiments

Different pH Condition of Isomerization

Except pH is changed before isomerization, other steps are carried out according to the operation described in embodiment 1, and the results are shown in the following table:

|  | pH adjusted by hydrochloric acid | Product purity (%) | Yield (%) |
| --- | --- | --- | --- |
| Embodiment 1 | 7-8 | 99.7 | 85.3 |
| Embodiment 2 | 5-6 | 99.4 | 84.6 |
| Embodiment 3 | 9-10 | 99.0 | 82.4 |
| example 1 of pH comparative experiment | 4.5-5 | 99.2 | 74.1 |
| example 2 of pH comparative experiment | 11.5-12 | 93.9 | 68.3 |

Conclusion: the purity and yield of product are higher when pH of isomerization is 5-10.

Embodiment 4-7

Different Catalysts for Isomerization

It's performed according to the operation described in embodiment 1 with catalyst changed only, and the results are demonstrated in the following table:

|  | Catalyst | Product purity (%) | Yield (%) |
| --- | --- | --- | --- |
| Embodiment 4 | Pd (OAc)$_2$ | 99.7 | 85.3 |
| Embodiment 5 | (Ph$_3$P)$_3$PdCl$_2$ | 99.4 | 83.5 |
| Embodiment 6 | (PhCN)$_2$PdBr$_2$ | 99.3 | 84.2 |
| Embodiment 7 | PdCl$_2$ | 99.3 | 83.7 |

Conclusion: the effects of these above catalysts for isomerization are all fine with high purity and yield of product.

Embodiment 8-10 and Example of Temperature Comparative Experiment

Different Isomerization Temperature

In accordance with the operation in embodiment 1, only isomerization temperature is changed, and the results are described in the following table:

|  | Temperature (° C.) | Product purity (%) | Yield (%) |
| --- | --- | --- | --- |
| Embodiment 1 | 50 | 99.7 | 85.3 |
| Embodiment 8 | 30 | 99.5 | 84.3 |
| Embodiment 9 | 60 | 99.5 | 85.1 |
| Embodiment 10 | 70 | 99.3 | 82.4 |
| example of temperature comparative experiment | 90 | 98.9 | 70.5 |

Conclusion: suitable isomerization temperature is 50-70° C.

Embodiment 11

Preparation of 3,7-dimethyl-9-(2,6,6-trimethylcyclohexene-1-yl)-2Z,4E,6E,8E-nonatetraenoic acid

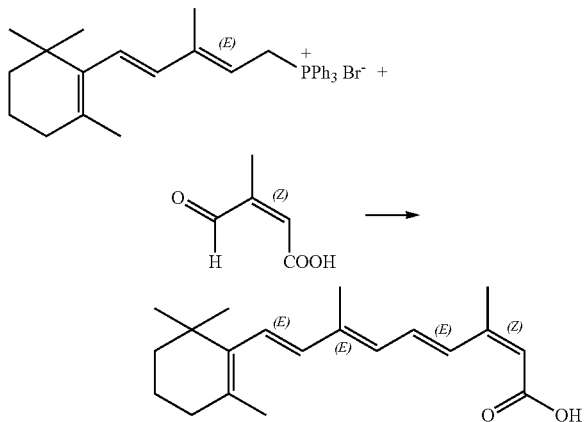

214 g [3-methyl-5-(2,6,6-trimethylcyclohexene-1-yl)-2E,4E-pentadiene]-triphenyl phosphonium bromide was dissolved into 650 ml isopropanol; 52.7 g cis-β-formyl crotonic acid was added with nitrogen filling; as the solution was stirred to be transparent, at 20-30° C., 652 ml NaOH isopropanol solution whose concentration is 2N was added dropwise, and keeping the temperature 20-30° C.; After reaction was performed for 3 hours, pH was adjusted to 7-8 by hydrochloric acid, and 102 mg palladium acetate was added with temperature increased to 60° C.; the reaction result was detected by HPLC; After isomerization was completed, the reaction liquid was poured into water, neutralized with NaOH, filtrated to gain crude product with suction filter, crystallized by ethyl acetate to obtain 98.9 g product with purity of 99.8% and yield of 86.3%.

Embodiment 12

Preparation of 3,7-dimethyl-9-(4-methoxy-2,3,6-trimethyl-phenyl)-2E,4E,6E,8E-nonatetraenoic acid

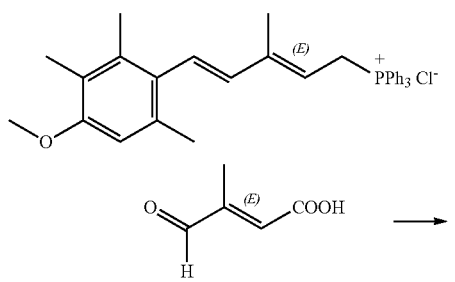

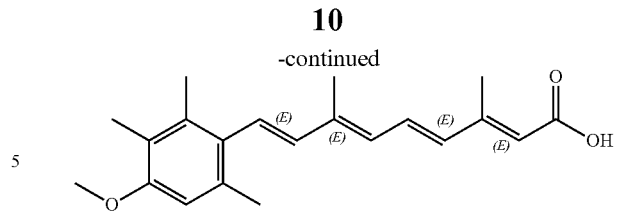

102 g [3-methyl-5-(4-methoxy-2,3,6-trimethyl-phenyl)-2E,4E-pentadiene]-triphenyl phosphonic chloride was dissolved into 395 ml isopropanol; 32.2 g trans-β-formyl crotonic acid was added with nitrogen filling; as the solution was stirred to be transparent, 363 ml KOH isopropanol solution whose concentration is 2N was added dropwise with temperature kept at −30-20° C.; After reaction was performed for 12 hours, pH was adjusted to 7-8 by hydrochloric acid, and 791 mg Pd(NH$_3$)$_2$Cl$_2$ was added with temperature increased to 30° C.; the reaction result was detected by HPLC; as isomerization was completed, the reaction liquid was poured into water, neutralized with concentrated hydrochloric acid, filtrated to gain crude product with suction filter, crystallized by ethyl acetate to obtain 52.4 g product with purity of 99.1% and yield of 85.2%.

Embodiment 13

Preparation of 3,7-dimethyl-9-(2,6,6-trimethylcyclohexene-1-yl)-2E,4E,6Z,8E-nonatetraenoic acid

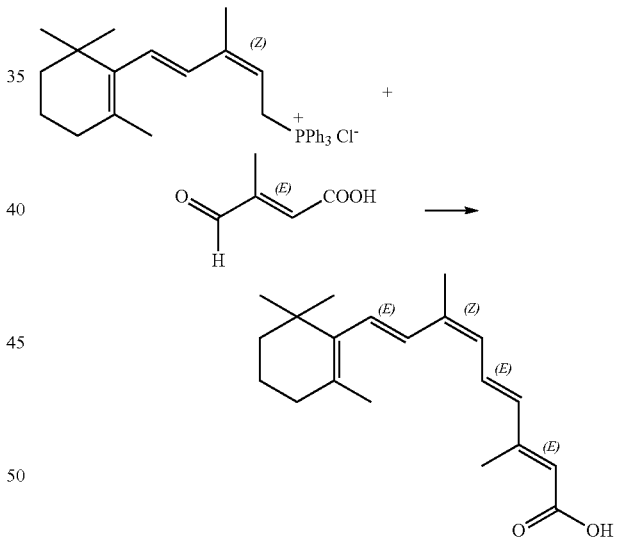

426 g [3-methyl-5-(2,6,6-trimethylcyclohexene-1-yl)-2Z,4E-pentadiene]-triphenyl phosphonic chloride was dissolved into 830 ml isopropanol; 75.4 g trans-β-formyl crotonic acid was added with nitrogen filling; as the solution was stirred to be transparent, at −50~−40° C., 752 ml NaOH isopropanol solution whose concentration is 2N was added dropwise with temperature kept at −50~−40° C.; After reaction was performed for 24 hours, pH was adjusted to 8-9 by hydrochloric acid, and 19 mg palladium acetate was added with temperature increased to 80° C.; the reaction result was detected by HPLC; After isomerization was completed, the reaction liquid was poured into water, neutralized with concentrated hydrochloric acid, filtrated to gain crude product with suction filter, crystallized by ethyl acetate to obtain 204.2 g product with purity of 99.8% and yield of 82.3%.

Effect Comparison Between the Processes of the Invention and References

The process in reference CN101774954 A

Preparation with 3 steps:

1. [3-methyl-5-(2,6,6-trimethylcyclohexene-1-yl)-2,4-pentadiene]-triphenyl phosphonium is adopted as raw material to react with β-formyl crotonicacid ester (Formula V) to carry out WITTIG reaction, and intermediate product is generated as mixture of 3,7-dimethyl-9-(2,6,6-trimethylcyclohexene-1-yl)-2,4,6,8 all trans nonatetraenoate (Formula VI) and its cis isomer (Formula VII);

Formula V

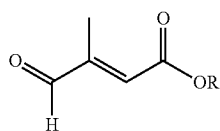

In Formula V, R is alkyl of $C_1$-$C_4$.

Formula VI

Formula VII

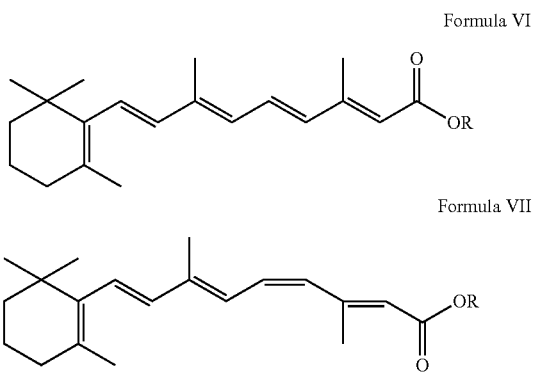

2. The above mentioned intermediate product is hydrolyzed to gain mixed acid;
3. The above mentioned mixed acid is conducted with isomerization configuration transformation to obtain end product of Formula I.

Although the process in reference CN101774954 A can solve the purity problem of stereo-isomers to get the desired all-trans product, it has multiple steps, and it requires intermediate separation with complex operation as well as long working hours, which makes loss of product. In particular, it's consuming time but incomplete in hydrolysis steps, so cost of this process is high yet with the highest total yield at 75%.

In the following table, the difference of processes between this invention and CN101774954A is compared with regard to preparing all-trans tretinoin (the above mentioned Formula I), which further illustrates technical effect of the invention.

Comparison between the invention and prior art

|  | Process in CN101774954 A | Process in the invention |
|---|---|---|
| Raw materials | [3-methyl-5-(2,6,6-trimethylcyclohexene-1-yl)-2,4-pentadiene]-triphenylphosphonium | [3-methyl-5-(2,6,6-trimethylcyclohexene-1-yl)-2,4-pentadiene]-triphenylphosphonium |

Comparison between the invention and prior art

|  | Process in CN101774954 A | Process in the invention |
|---|---|---|
| Reaction steps and features | (Formula II) β-formyl crotonic acid ester (Formula V) 1. carrying out WITTIG reaction under the action of alkali to gain mixture with two esters (Formula VI and Formula VII); 2. hydrolyzing, obtain mixed acid; 3. performing isomerization configuration transformation to obtain end product. The product of WITTIG reaction 3,7-dimethyl-9-(2,6,6-trimethylcyclohexene-1-yl)-2,4,6,8 all trans nonatetraenoate (Formula VI) and its cis isomer (Formula VII) is required to be separated. Hydrolysis is required Its unsuitable for industrial production due to multiple steps and high cost. | (Formula II) β-formyl crotonic acid (Formula III) carrying out WITTIG reaction under the action of alkali; obtaining directly mixed acid by adding acid; adding catalyst to perform isomerization to gain end product. The product of WITTIG reaction is not required to be separated; Hydrolysis is not required; Since no intermediate separation is required, three steps are carried out continuously in one container, which is suitable for industrial production. |
| Before isomerization, the pH of reaction liquid adjusted to | 3.5-4.5 | 5-10 |
| Isomerization transformation ratio | 80-83% | 92-95% |
| Total reaction time (counted according to industrial production) | 55-60 hours | 25-30 hours |
| Total yield | 75% | 85% |
| Total cost (RMB Yuan/kg) | 5600 | 3150 |

The invention claimed is:

1. A process for preparing compound of the Formula I comprises: performing WITTIG reaction under the action of alkali with the substituted tri-phenyl phosphonate (Formula II) and β-formoxyl crotonic acid (Formula III) as raw materials; then performing isomerization by adding palladium compound or rhodium compound to obtain the product compound of Formula I with desired configuration, characterized in that:

1) there is no need to perform hydrolysis after the WITTIG reaction;
2) there is no need to separate the products of WITTIG reaction, but performing isomerization directly; the WITTIG reaction and the isomerization are conducted continuously in one container;
3) adjusting the pH of reaction liquid to 5-10 by adding acid before the isomerization;

Formula I

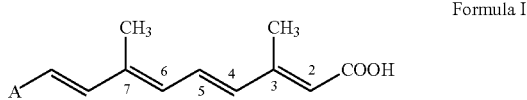

in Formula I, the carbon-carbon double bonds on site 2-3, site 4-5 and site 6-7 have cis or trans configuration;

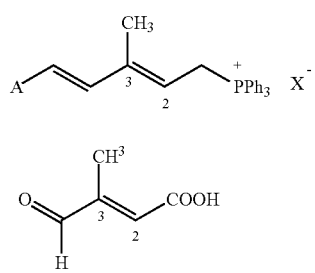

Formula II

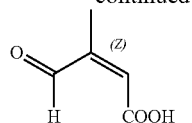

Formula III in Formula II and Formula III, the carbon-carbon double bonds on site 2-3 have cis or trans configuration;

in Formula I and Formula II, A is substituted unsaturated hexatomic carbocyclic group; X is selected from Cl, Br or $HSO_4$.

2. The process as claim 1, wherein Formula I and Formula II, A is 2,6,6-trimethylcyclohexenyl or 2,3,6-trimethyl-4-methoxyphenyl.

3. The process as claim 2, wherein the configuration of said raw materials and the products is selected from the following 4 configurations:

1) the raw material Formula II is the compound of Formula IIa; the raw material Formula III is the compound of Formula Ma; the product Formula I is the compound of Formula Ia:

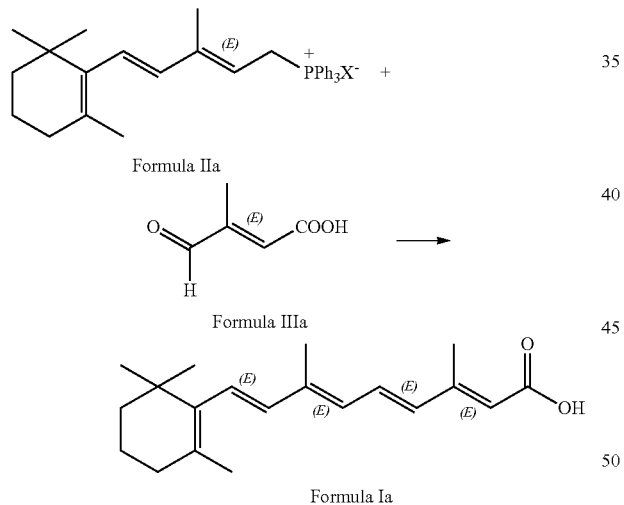

Formula IIa

Formula IIIa

Formula Ia 2) the raw material Formula II is the compound of Formula IIa; the raw material Formula III is the compound of Formula Mb; the product Formula I is the compound of Formula Ib:

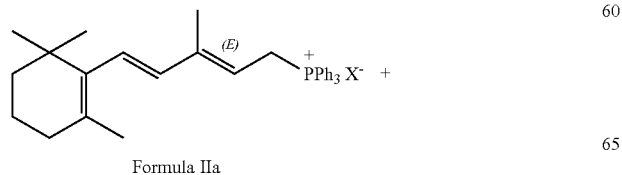

Formula IIa

-continued

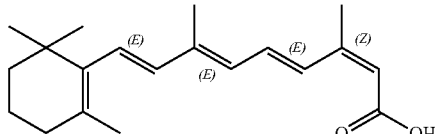

Formula IIIb

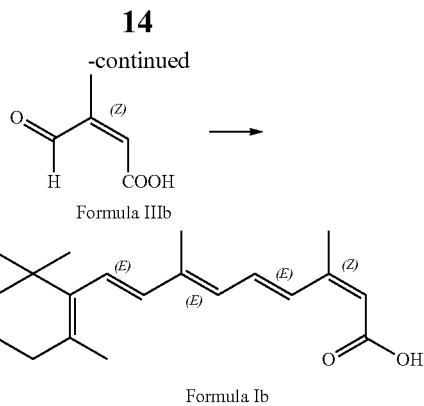

Formula Ib 3) the raw material Formula II is the compound of Formula IIc; the raw material Formula III is the compound of Formula Ma; the product in Formula I is the compound of Formula Ic:

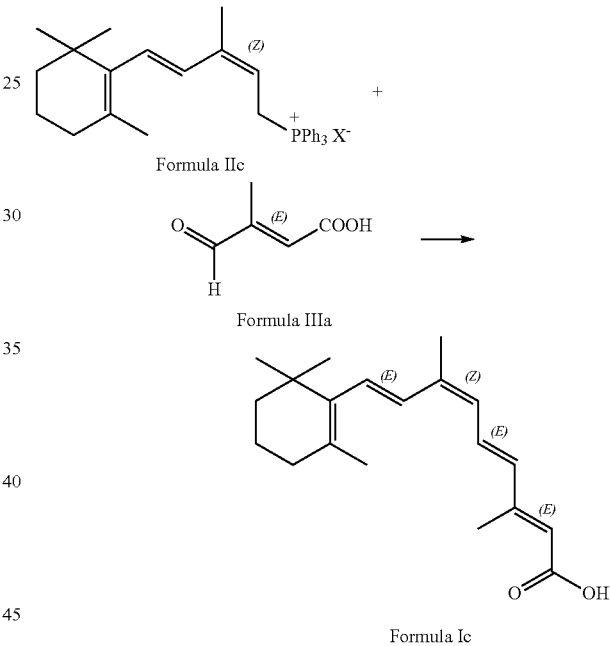

Formula IIc

Formula IIIa

Formula Ic 4) the raw material Formula II is the compound of Formula IId; the raw material Formula III is the compound of Formula Ma; the product in Formula I is the compound of Formula Id:

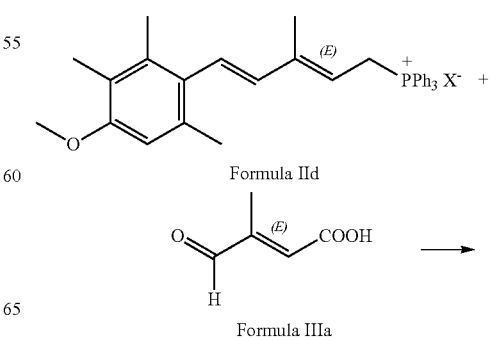

Formula IId

Formula IIIa

-continued

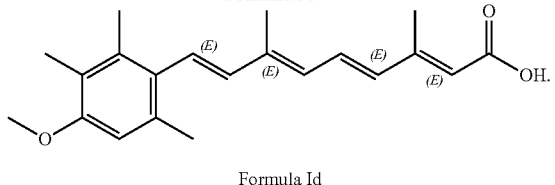

Formula Id

4. The process as claim 1, wherein molar ratio between the compounds of Formula II and Formula III is 1:0.8-1.5.

5. The process as claim 1, wherein the alkali is alkaline metal salt of $C_1$-$C_6$ alkyl alcohol or metal hydroxide.

6. The process as claim 1, wherein adjusting the pH of reaction liquid to 7-8 by adding acid before isomerization; said acid is selected from sulphuric acid, hydrochloric acid, phosphoric acid, hydrobromic acid or $C_1$-$C_6$ alkyl acid.

7. The process as claim 1, wherein the palladium compound or rhodium compound is selected from $PdCl_2$, $PdBr_2$, $PdI_2$, $PdF_2$, PdS, $(CH_3CN)_2PdCl_2$, $Pd(OAc)_2$, $(PhCN)_2PdCl_2$, $Pd(NO_3)_4(NH_4)_2$, $Pd(NH_3)_2Cl_2$, $PdS_2$, $K_2PdCl_6$, $Pd(NH_3)_2(NO_2)_2$, $Pd(NO_2)_4(NH_3)_2$, $(PhCN)_2PdBr_2$, $(NH_4)_2PdCl_4$, $(NH_4)_2PdCl_6$, $(Ph_3P)_4Pd(0)$, $(Et_3P)_4Pd(0)$, $(Ph_3P)_3PdCl_2$, $Pd(NO_3)_2+Ph_3P$, $Pd(OAc)_2$; molar ratio between the palladium compound or rhodium compound and compound in Formula II is 0.0001-0.02:1.

8. The process as claim 1, wherein the palladium compound is palladium acetate.

9. The process as claim 1, wherein temperature of WITTIG reaction is −50° C.-30° C.

10. The process as claim 1, wherein temperature of isomerization is 30° C.-80° C.

* * * * *

UNITED STATES PATENT AND TRADEMARK OFFICE
CERTIFICATE OF CORRECTION

| | | |
|---|---|---|
| PATENT NO. | : 8,835,680 B1 | Page 1 of 1 |
| APPLICATION NO. | : 14/117343 | |
| DATED | : September 16, 2014 | |
| INVENTOR(S) | : Deng et al. | |

It is certified that error appears in the above-identified patent and that said Letters Patent is hereby corrected as shown below:

On the Title Page, Item (57), under "ABSTRACT", in Column 2, Line 9, delete "dose" and insert -- does --, therefor.

In the Specification

In Column 4, Line 21, delete "the" and insert -- The --, therefor.

In Column 4, Line 35, delete "NH4)2" and insert -- (NH4)2 --, therefor.

In Column 6, Line 44, delete "reaction reaction," and insert -- reaction, --, therefor.

In the Claims

In Column 13, Line 29, in Claim 3, delete "Ma;" and insert -- IIIa; --, therefor.

In Column 13, Line 56, in Claim 3, delete "Mb;" and insert -- IIIb; --, therefor.

In Column 14, Line 19, in Claim 3, delete "Ma;" and insert -- IIIa; --, therefor.

In Column 14, Line 19, in Claim 3, delete "Ma;" and insert -- IIIa; --, therefor.

Signed and Sealed this
Seventh Day of April, 2015

Michelle K. Lee
*Director of the United States Patent and Trademark Office*